United States Patent

Veronikis

Patent Number: 5,681,340
Date of Patent: Oct. 28, 1997

[54] VAGINAL DILATOR

[75] Inventor: Dionysios K. Veronikis, Watertown, Mass.

[73] Assignee: BEI Medical Systems, Inc., Hackensack, N.J.

[21] Appl. No.: 637,618

[22] Filed: Apr. 25, 1996

[51] Int. Cl.$^6$ ........................................ A61B 17/00
[52] U.S. Cl. ............................................. 606/191
[58] Field of Search ......................... 606/1, 191, 197; 604/42, 39

[56] References Cited

U.S. PATENT DOCUMENTS

| | | | |
|---|---|---|---|
| 876,775 | 1/1908 | Crittenden | 606/191 |
| 1,551,499 | 8/1925 | Homan | 606/197 |
| 2,721,549 | 10/1955 | Ferraro | 606/191 |
| 3,587,588 | 6/1971 | Murr | 606/191 |
| 3,698,391 | 10/1972 | Mahony | 606/191 |

Primary Examiner—William Lewis
Attorney, Agent, or Firm—Allen A. Dicke, Jr.

[57] ABSTRACT

The adjustable variable length vaginal dilator is assembled from selected parts of parts of various length so as to achieve a selected desired length, and at least two of the parts are threaded. The distal threaded joint secures a selected length tip and the proximal adjustable threaded base provides infinite length adjustments between the main body coupler and the base. An intermediate extender may also be used for added length. The dilator permits self-treatment sessions over a long period of time that permits slow small interval stretching with maximum patient comfort. Another embodiment provides a tapered transition section and a tip of smaller diameter which is also of selectable length for more comfort during therapy and the like.

22 Claims, 3 Drawing Sheets

VAGINAL DILATOR

FIELD OF THE INVENTION

This invention is directed to a vaginal dilator made up of parts of selected length to provide a length-adjustable appliance.

BACKGROUND OF THE INVENTION

There are a number of medical reasons for having a vagina of inadequate length. Vaginal agenesis occurs in patients born completely without a vagina or with an underdeveloped vagina. In other cases, a normal vagina may have been shortened due to surgery for benign disease or to remove a cancerous condition. In other patients, the vagina has been surgically removed.

When surgical procedures are used in the construction of a neovagina, a steady constant contraction of the newly created underlying tissue bed by and from the formation of scar tissue over time may result in inadequate length. Also, in surgical construction, agglutination of the upper walls of the newly constructed vagina by coaptation may occur. Thus, it is useful to provide a vaginal dilator of selectable length which is useful following surgery to prevent the vaginal walls from becoming agglutinated. It is also desirable to provide a vaginal dilator of selectable diameter and length adjustability to permit maintaining the length and/or stretching the length of a vagina which may have been shortened due to surgery, scar tissue, or non-use of a neovagina.

SUMMARY OF THE INVENTION

The vaginal dilator of this invention is made up of parts selected from a group including multiple tips, couplers, and bases, a coupler extender as well as selectively included spacer washers so that the dilator can be assembled to a selected length. At least a the base of the group of parts is screw-threaded for infinite length adjustment. Thus, the vaginal dilator can be assembled to various lengths so as to provide infinite adjustment of length of dilation for different therapeutic purposes. In addition, an initial tip of smaller diameter and selectable length may be attached with a partial or full tapered transition coupler section and ase with or without the intermediary coupler extender.

It is, thus, a purpose and advantage of this invention to provide a vaginal dilator which is of selectable length so that it can be assembled from selected parts to provide dilation and/or vaginal wall opposition in different therapeutic situations.

It is a further purpose and advantage of this invention to provide a vaginal dilator which has a tip and a base and/or a tip-coupler-base assembly or a tip-coupler-extender-base assembly and has screw-threaded adjustments between the tip and the base, coupler and the base, as well as the extender and the base so as to provide infinite adjustment of length.

It is a further purpose and advantage of this invention to provide a vaginal dilator which can be employed in a self-treatment session wherein the patient achieves vaginal stretching force by sitting, the force generated by the patient's weight on the dilator and multiple concomitant intrasession as well as inter-session adjustments to the length of the dilator, or to the diameter of the tip or to the tpered transition coupler section, will achieve slow and comfortable stretching.

It is another purpose and advantage of this invention to provide an independent vaginal dilator which is easily portable and inexpensive so that it can be used widely by patients, even those who travel frequently, over long periods of time to maintain a functional organ.

It is another purpose and advantage of this invention to provide a vaginal dilator which includes a tapered transition section so that a tip of smaller diameter and selectable length may be used for initial therapy. The tper will end with the dimeter of the standard diameter coupler. This permits selectability of tip diameter as well as length to regulate dilation diameter and/or slow and comfortable stretching. The tapered transition section provides an additional measure to facilitate and regulate slow and comfortable stretching.

Other purposes and advantages of this invention will become apparent from a study of the following portion of the specification, the claims and the attached drawings.

DESCRIPTION OF THE PREFERRED EMBODIMENTS

Figure 1:
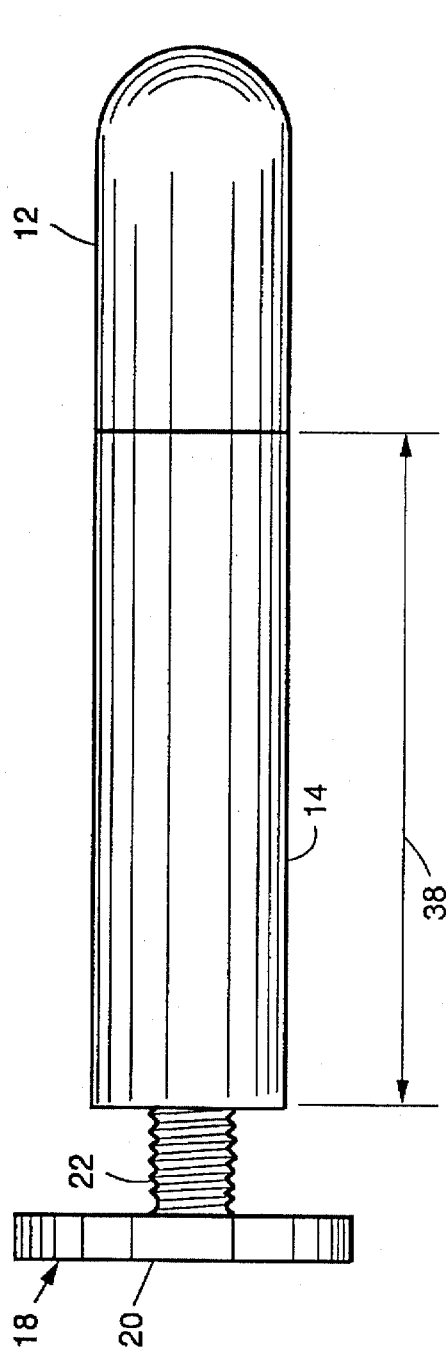
FIG. 1 is a side-elevational view of a vaginal dilator in accordance with this invention assembled from a plurality of different parts of selected length, such as may be selected for day-time therapy purposes.

The vaginal dilator of this invention is a patient assembled appliance and is made up to a desired length by assembling together selected parts of different lengths. The first preferred embodiment of the assembled vaginal dilator 10 is shown in FIG. 1 and is assembled for one purpose of the selected parts shown in exploded view in FIG. 2. The vaginal dilator 10 is made up of tip 12, coupler 14 and base 18. There are other parts which can be chosen to assemble a dilator of different length, as is discussed below. The base 18 has a baseplate 20 and a threaded shank 22 of length 24. Tip 12 has a length of dimension 26 and has a hemicylindrical, rounded nose on the tip corresponding in diameter to the circular diameter of tip 12. A preferred diameter is about 1 inch, but other diameters are not excluded.

Figure 2:
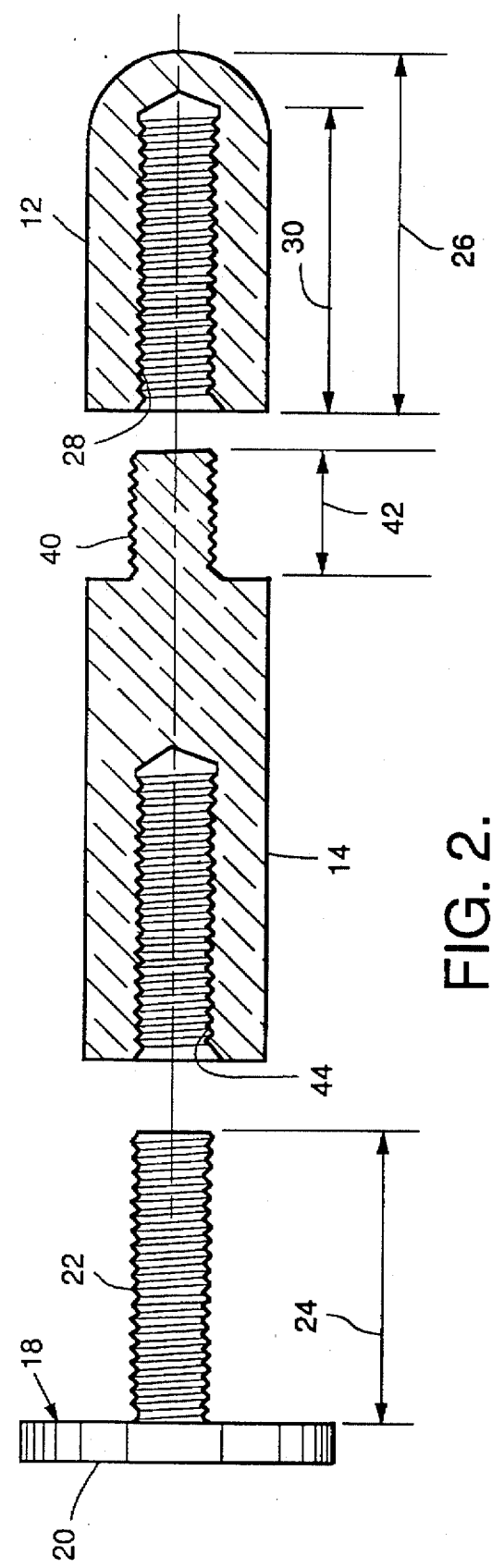
FIG. 2 is an exploded view thereof, with parts broken away and parts taken in section.

Tip 12 has a threaded recess 28 which has a length 30. The threaded shank 40 is sized to thread into recess 28. The threaded recess 28 has the same size threads as the threaded shank 22 and the threaded shank 40 on coupler 14. As is seen in FIG. 2, the length 24 of the threads 22 on the base are longer than the threads 40 on the coupler. The threaded depth 30 in the tip 12 is at least as long as the length 24 so that the base can be threaded into the tip for purposes which are described below. The threaded recess 44 in coupler 14 is also sized to fit the threads 22. Rotation of the threaded engagement of the base into the coupler 14 can lengthen the overall length of the dilator from the rounded nose of the tip to the left end of the baseplate 20 in infinitely small increments. The selection of tip 12 and base 18, threaded together, provides the shortest length of tip and base of selected parts which can be used together as the vaginal dilator without a coupler in accordance with this invention.

Figure 5:
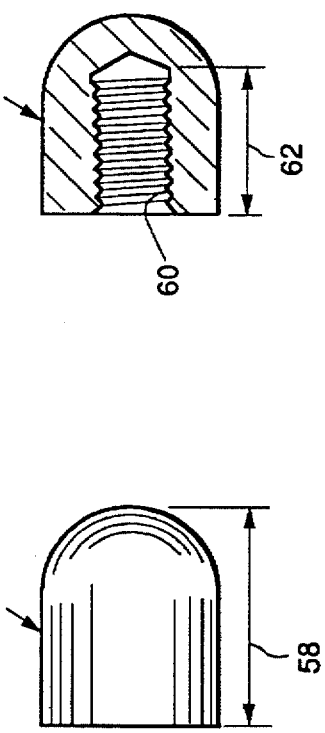
FIG. 5 is a side-elevational view of another length tip available for selection to be used in the dilator.

During treatment sessions, as described below, the length of the dilator will be increased by turning out the base on its threads. When the baseplate 20 has been rotated and dialed out 2 centimeters, the tip may be exchanged for one that is 2 centimeters longer, the baseplate is turned back to its fullest extent and the process continues. Different lengths of tips are shown in FIGS. 3 and 5 and will be described below.

Figure 3:
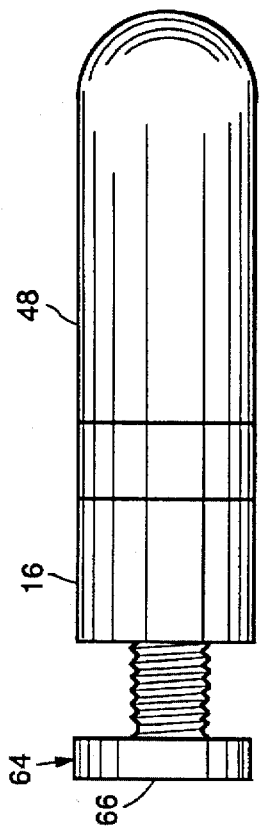
FIG. 3 is another view of the vaginal dilator of this invention assembled from parts of a different length, such as preferably would be chosen for night-time maintenance, with parts broken away and parts taken in section.
Figure 4:
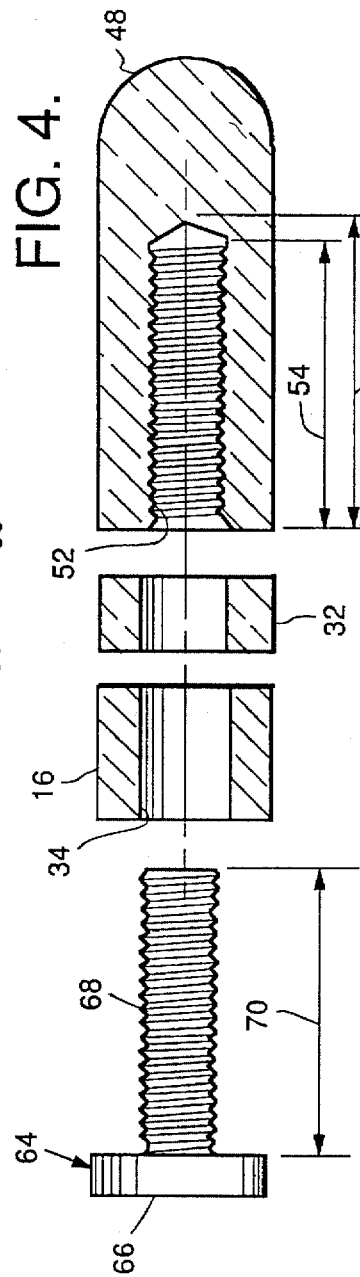
FIG. 4 is an exploded view thereof, with parts broken away and parts taken in section.

To choose a vaginal dilator for night-time therapy, spacers 16 and/or 32, seen in FIGS. 3 and 4, may be selected and used with base 66 and tip 48. This is an example of an assembly of current suitable for night-time dilation maintenance. Spacer 16 has the same cylindrical outer diameter as the tip 12 and has an inner bore 34 which is large enough to clear the threads in the shank 65 of base 64. The spacer 16 has a length 36, as seen in FIG. 3. The spacer 32 is the same, except for its length 38, which is about half the length 36. Either one or both of the spacers can be placed onto the shank 68. As a particular example, spacer 16 may be 2 centimeters long, while spacer 32 may be 1 centimeter long. Either one or both of these spacers may be used with one of the selected tips. Thus, three additional lengths of the vaginal dilator can be selected by use of one or both of the spacers 16 or 32. When night-time therapy is desired, the small base 66 is chosen so that the appliance is completely within the vagina. The large base and a selected tip without a coupler provide the shortest length for active adjustable day-time stretching therapy.

It can be appreciated that, for day-time therapy sessions, additional length selections may be accomplished by including other selected parts in the assembled dilator. For example, coupler 14 can be included. Coupler 14 is a cylindrical body of the same diameter as the tip. The coupler 14 has a length 38 which is preferably greater than the sum of the lengths of the two spacers 16 and 32. The coupler 14 has a threaded shank which has a length 42, see FIG. 2, which is less than the length 30. The threaded shank has threads which threadedly engage in the threaded recess 28. The coupler 14 has a threaded recess 44 which has a length 46, which is long enough to receive the threaded shank 22 of length 24. Thus, a dilator can be assembled with tip 12, coupler 14, and base 18 without using any spacers.

In addition to these selections of fixed length, as described above, the base can be threaded into the coupler a selected distance so that the overall length from tip to bottom of base can be selected over an infinite set of steps within the adjustment limit. This is not a pre-therapy designated length, but is a dynamic length value which changes during each therapy session. The length may change by a number of increases, then a decrease only to be followed by another increase prior to ending the therapy session.

Other options also exist for choosing an assembled length of the vaginal dilator. Tip 48, shown in FIGS. 3 and 4, is the same as tip 12 except it extends to a greater length 50. It contains therein bore 52, which has a length 54, which has appropriate threads and is long enough to receive the shank 22. The length 54 is preferably equal to length 30 and is at least as long as the length 70. Thus, the length 50 is longer than the length 26. The selection of tip 48 rather than tip 12 places another increment of length which is available for selection.

Figure 6:
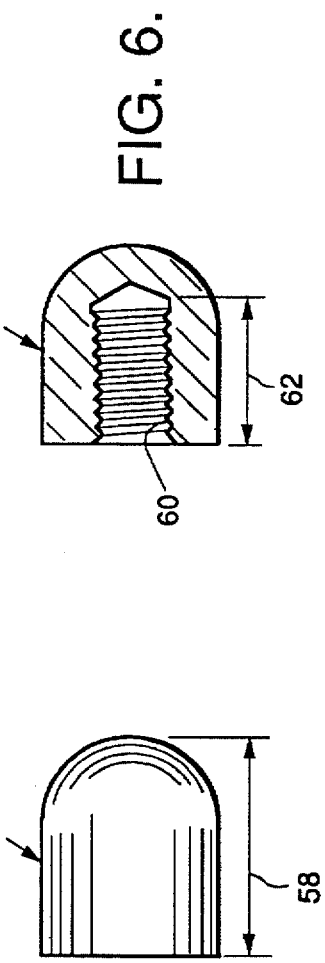
FIG. 6 is a longitudinal section therethrough.

Tip 56 is shown in FIGS. 5 and 6. It is the same as the other tips, except that it has a length 58 and has a threaded recess 60 therein which has a length 62. The bore is long enough to receive the threaded shank 40 on the coupler 14. The threaded recess 60 has threads therein to receive the threads on the coupler. Selection of tip 58 with spacers 16 and 32 provides the shortest length of full diameter selected parts for night-time intra-vaginal therapy.

In addition to the selection of full sized dilator parts, there is a selection between the full sized base 18 shown in FIGS. 1 and 2 and the smaller diameter base 64 seen in FIGS. 3 and 4. The base 18 has a large diameter baseplate 20. As is described below, the dilator can be employed while sitting. The baseplate 20 engages upon the chair and, thus, it is convenient to have a baseplate of larger diameter than the shank diameter of the remainder of the dilator. However, this larger baseplate may be uncomfortable during sleeping. For this reason, the base 64 has a baseplate 66 which is of the same diameter as the diameter of the selected tip. Base 64 can also be used for therapy to engage upon the chair. This variation on selection is again for patient selection and comfort. The threaded shank 68 has the same threads on it to threadedly engage into threaded recess 28, 44, 52 or 60. Its length 70 is the same as the length 24. The base 64 can be therapeutically employed while sleeping, standing and walking without the potential for discomfort caused by the larger baseplate.

Figure 7:
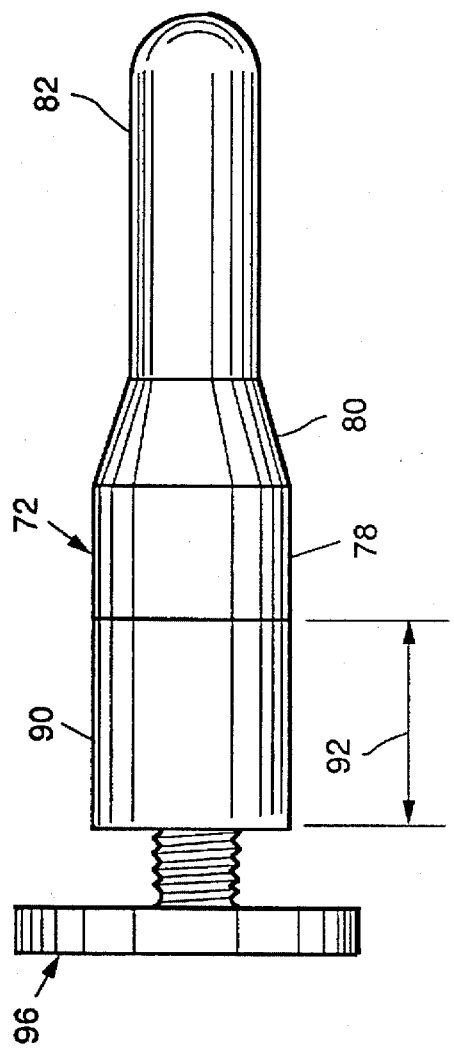
FIG. 7 is a side-elevational view of a second preferred embodiment of the vaginal dilator in accordance with this invention assembled from a plurality of different parts, including a tapered transition section, a coupler extender and a tip of smaller diameter.
Figure 8:
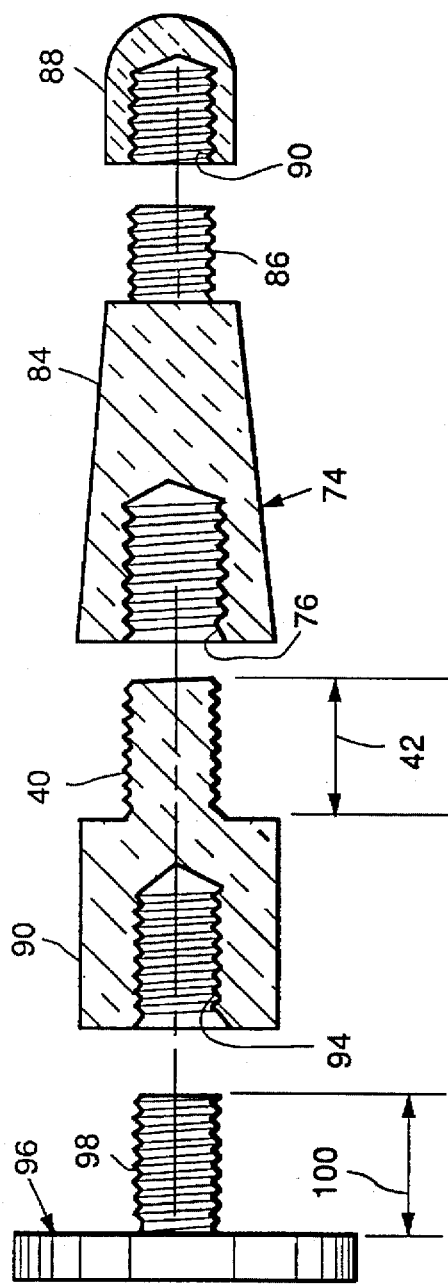
FIG. 8 is an exploded view of a vaginal dilator similar to that of FIG. 7, but employing a different shape of tapered transition section and a different length of small diameter tip.

The vaginal dilator assemblies shown in FIGS. 7 and 8 employ coupler 90 which is similar to coupler 14. Since the coupler 90 has a length 92 which is shorter than the length 38 of coupler 14; for example 3 centimeters, the internal threads 94 are of shorter length; for example 13/16th inch deep. Similarly, base 96 is similar to base 18. The baseplate is the same diameter, but the threaded shank 98 is a shorter length 100 to be accepted by the internal threads 94. The coupler 90 and base 96 can be used as part of the group from which parts are selected in accordance with the principles described above.

To provide further selectability, this time including a reduced diameter, tapered transition sections 72 and 74 are provided. As seen in FIG. 8, transition section 74 has internal threads 76 which fit onto the threaded shank 40. The transition section 72 has the same internal threads therein. The tapered transition sections each have a base diameter equal to the diameter of coupler 94. Transition section 72 has a straight portion 78, the same diameter as coupler 90, and a tapered portion 80 which tapers down to the diameter of tip 82. The tapered transition section 74 is the same, except that its tapered portion 84 extends its entire length from the large end of the cone, which is the diameter of coupler 90, to the conical truncated diameter of the tip 82. Both of the transition sections are truncated cones with axes on the thread axis. The two transition sections thus have the same function and may be the same length.

Each of the transition sections has a male threaded shank thereon with a threaded shank 86 shown in section 74. The external threads on the threaded shank are sized so that the tip 82 or the tip 88 may be threaded thereon. Each of the tips has an internal threaded recess 90 which permits it to be screwed onto the shank 86. Two lengths of tip are illustrated in the tips 82 and 88. Other lengths may be made available, as is discussed below.

The tapered transition sections 72 or 74 may be used with a tip selected from a group of different lengths; for example, either the tips 82 or 88. Furthermore, the tapered transition sections can be used with coupler 90 to achieve greater length. This provides the option for creation of a narrower initial pilot neovagina which may be dilated with greater comfort and enhanced further dilation of the larger diameter by the tapered transition coupler, which achieve full diameter stretching proximal of the tapered transition coupler.

Purely as a matter of example, all of the parts of the vaginal dilator can be made of a high-grade synthetic polymer composition material such as polycarbonate. A preferred main diameter is 1 inch, although it may be larger or smaller for particular situations. All of the parts are cylindrical about a central axis. The threaded shanks and threaded recesses are on the same axis and have the same threads. As an example of preferred dimensions, the lengths 24 and 70 are about 1 9/16 inch. The corresponding threaded recesses 28, 44 and 54 have a depth about 1 5/8 inch in order to receive those shanks. The length 38 of coupler 14 can be 7 centimeters. The lengths 36 and 37 of the two spacers may be 2 centimeters and 1 centimeter, respectively. The lengths 58, 26 and 50, respectively, of the tips 56, 12 and 48 may be 3 centimeters, 5 centimeters and 7 centimeters, respectively. The length 62 of the threaded recess 60 may be 7/8 inch, and the length 42 of the corresponding shank 40 may be 3/4 inch. These various parts permit assembly of a vaginal dilator of the appropriate length in centimeter increments from 5 centimeters to 14 centimeters. Each also provides additional infinite length adjustment by rotating the base with respect to the coupler or tip into which it is threaded to provide infinitely variable screw-thread adjustment.

The diameter of the main structure shown in FIGS. 1 through 6 is preferably 1 inch, as described above. The reduced diameter tips 82 and 88 are preferably about 5/8 inch diameter. Of course, the truncated transition sections have that diameter at their smaller, truncated end. The tips 82 and 88 are preferably selected from a set of five tips of a length of 1.5 centimeters, 2.5 centimeters, 3.5 centimeters, 4.5 centimeters and 5.5 centimeters. Each of these tips has a hemispherical distal end. The thread 86 is preferably about 1 centimeter long. In this way, an additional choice of tip diameter and tip length can be made for optimum dilation treatment.

Typical treatment is for patients during the healing phase after surgical construction of a neovagina, as well as the maintenance of the neovagina. Additionally, patient self-creation or self-recreation may be facilitated by the smaller diameter tips and tapered transition sections through at tmes unusually dense scar tissue. In this respect, an initial pilot neovaginal canal is created which is easily dilated further. If the patient is going to take the treatment while seated, she selects the most comfortable base, usually the one with the larger baseplate, and selects the appropriate diameter and length tip together with a choice of whether or not a coupler and/or extender will be employed. The base may or may not be fully threaded in at the start of treatment. For example as shown in FIG. 1, the base is dialed out. The dilator is inserted, and the patient is seated. If correctly chosen, the tip of the dilator will exert just a mild stretch to the top of the vagina. After initial accommodation and during the treatment session, the length of the dilator will be increased over several minutes by turning out the base. This is an adjustable dial effect which can be easily accomplished by turning the base, once slightly raised. The adjustment can be as little as 1 millimeter or as much as 2 centimeters, and it is entirely up to the patient who determines how much stretching is required or can be tolerated.

This typical treatment session applies to patients during the healing phase after surgical construction of a neovagina during the maintenance of the neovagina as well as to the creation or recreation of a neovagina shortened by scarring. For example, should the patient in later years discover that the vagina has lost some length thereby causing discomfort, she can regain that length by using the vaginal dilator of this invention by increasing its length during therapy sessions. The variable length adjustable dilator is easily and readily concealed in a woman's purse allowing therapy during business trips, vacations or any prolonged visit away from home without compromising privacy or therapy. It serves as a therapeutic device that may be privately carried by the patient for many years and used as needed. Patients with a surgically shortened vagina would use the appliance in the same manner to regain length. The vagina is an organ which has a tremendous capacity to stretch, and it is this capability which permits the vaginal dilator of this invention to create lengthening.

The variable length vaginal dilator of this invention is capable of adapting to thin as well as obese patients because the overall length of the dilator is the length from the tip to the seat of the chair. The patient will be sitting normally in a chair with a variable length of dilator in position. The length is then increased, as required, by slighting getting up from the chair and turning the base which rests upon the chair seat while in use. Due to its selectable parts to achieve variable length as well as the screw-threaded adjustment base, the variable length adjustable vaginal dilator of this invention is not only capable of adjusting to the stretch distance required in the surgically shortened vagina and as adjunct therapy to the surgically constructed neovagina, but also is a primary treatment in patients born without a vagina or in patients where the vagina has been surgically removed. The principles of treatment are the same. Construction of a neovagina is facilitated and comfort is enhanced for some patients by employing the transition sections and smaller tips shown in FIGS. 7 and 8. These are more likely to be used early in the treatment or many years later if length has been lost and may also be used during sleep hours.

The versatility is in the variable length that is achieved by the turning out of the base to increase the length. Choosing the appropriate length parts allows it to be used by patients who have shorter or longer stretch distance requirements, depending on their primary or secondary treatment modality as well as their stage of therapy. As the vagina gains length, different appliance components are chosen and installed in the vaginal canal to maintain the new stretch distance without extending the adjustment of the threaded base more than 2 centimeters, which is easily measured by the spacer 16a. In the case of the tapered transition coupler and narrower tip, the maximum base dial-out distance is 1 centimer and is measured with spacer 32, see FIG. 4. Thus, the variable length adjustable appliance is very versatile. It is a patient-controlled therapeutic device that fills a need in the non-surgical management of vaginal stretching. It is also useful as a post-surgical therapy of patients with very unique problems, while maintaining privacy and dignity.

This invention has been described in its presently contemplated best embodiment, and it is clear that it is susceptible to numerous modifications, modes and embodiments within the ability of those skilled in the art and without the exercise of the inventive faculty. Accordingly, the scope of this invention is defined by the scope of the following claims.

What is claimed is:

1. A vaginal dilator comprising:

a plurality of dilator tips each having a different length and/or diameter, each said dilator tip having a tip end surface, means on each said dilator tip for attachment; and a base having a baseplate, means on said base for adjustably attaching said tip on said base by cooperation with said attachment means on said tip so that a single tip can be selected from said plurality of dilator tips and adjustably attached to said base so that the distance between said tip end surface and said baseplate can be adjusted to adjust the therapeutic length of said dilator.

2. The vaginal dilator of claim 1 wherein said attachment means is a threaded attachment means so that said base is threadedly adjustable with respect to said tip so that rotation of said base with respect to said tip adjusts the length of said dilator between said tip end surface and said baseplate.

3. The vaginal dilator of claim 1 wherein there is also a spacer included in said vaginal dilator.

4. The vaginal dilator of claim 1 wherein said tip has an axis and said tip end surface is a circular cylindrical surface about said axis and has a curved tip end surface thereon.

5. The vaginal dilator of claim 4 wherein said tip has threads thereon about said axis and said base has threads thereon about said axis so that said base and said tip can threadedly interengage and the length between said tip end surface and said baseplate can be adjusted by rotation of said base with respect to said tip to make a threaded adjustment.

6. The vaginal dilator of claim 5 wherein said tip has a threaded recess thereon and said base has a threaded shank thereon which interengage to adjust said base with respect to said tip.

7. The vaginal dilator of claim 6 further including a coupler between said tip and said base, said coupler threadedly engaging said tip and said base threadedly engaging said coupler so that said coupler provides a longer length between said tip end surface and said baseplate.

8. The vaginal dilator of claim 1 further including a coupler between said tip and said base, said coupler threadedly engaging said tip and said base threadedly engaging said coupler so that said coupler provides a longer length between said tip end surface and said baseplate.

9. The vaginal dilator of claim 8 wherein said coupler has an axis and said threaded surfaces on said coupler are surfaces around said axis and the external surface of said coupler is a cylindrical surface about said axis with the same diameter as said tip.

10. A vaginal dilator comprising:

a dilator tip selected from a group of dilator tips of different length and/or diameter, said tip having an end surface;

a base having a baseplate;

means on said tip and on said base for adjustably and detachably attaching said tip on said base so that the distance between said tip end surface and said base plate can be adjusted to adjust the therapeutic length of said dilator; and a spacer included in said vaginal dilator between said base and said tip, said spacer being selected from a group of spacers of different length.

11. The vaginal dilator of claim 4 wherein said base is threadedly adjustable with respect to said tip so that rotation of said base with respect to said tip adjusts the length of said dilator between said tip end surface and said baseplate.

12. A vaginal dilator comprising:

a dilator tip selected from a group of dilator tips of different length and/or diameter, said tip having a tip end surface, said tip having an axis and said tip having a cylindrical surface about said axis and said tip having a curved tip end surface thereon, said tip having a threaded recess with threads therein, said recess being circular about said axis;

a base having a base plate, said base having an axis and having threads thereon about said axis so that said base and said tip can threadingly interengage and the length between said tip end surface and said base plate can be adjusted by rotation of said base with respect to said tip to make a threaded adjustment so that the distance between said tip end surface and said base plate can be adjusted to adjust the therapeutic length of said dilator; and a coupler between said tip and said base, said coupler having threaded surfaces thereon and said coupler threadedly engaging said tip and said base so that said coupler provides a longer length between said tip end surface and said base plate, said coupler having an axis and said threaded surfaces on said coupler are surface around said axis and the external surface of said coupler is a cylindrical surface about said axis with the same diameter as said top.

13. A vaginal dilator comprising:

a dilator tip selected from a group of dilator tips of different length and/or diameter, said tip having an end surface, said tip having an axis and said tip having an external surface which is a circular cylindrical surface about said axis and said tip end surface being a curved tip end surface, said tip having a threaded recess therein;

a tapered transition section, said tapered transition section having a threaded shank thereon, said tip being mounted on said shank of said tapered transition section, said tip on said tapered transition section being selected from a group of tips of different lengths, said taperered transition section having a female threaded portion; and a base having a base plate, said base having a threaded shank thereon sized to threadingly engage in said female threaded portion of said tapered transition section so that the distance between said tip end surface and said base plate can be adjusted to adjust the therapeutic length of said dilator.

14. The vaginal dilator of claim 13 wherein said tapered transition section has an exterior surface in the shape of a truncated cone with the conical axis substantially on the axis of said threaded shank.

15. The vaginal dilator of claim 13 wherein said tapered transition section threadedly engaging said tip and said base threadedly engaging said section provides a longer length between said tip end surface and said baseplate than without said coupler.

16. The vaginal dilator of claim 13 wherein said tapered transition coupler and said tip are threadedly engaged to said extender and said tip are threadedly engaged to said extender, and said extender threadedly engaging said coupler as well as threadedly engaging said baseplate so that said extender provides a longer length of tapered transition coupler and said baseplate can be adjusted by rotation of said base with respect to extender coupler and tip to make a threaded adjustment.

17. A vaginal dilator comprising:

a plurality of tips, each tip in said plurality of tips having a substantially cylindrical exterior surface and having an axis, each said tip in said plurality of tips having a curved tip end surface and having an attachment end opposite said curved tip end surface, each tip in said plurality of tips having a different length between said curved end surface and said attachment end, each tip in said plurality of tips having a threaded surface extending generally axially of said tip; and a base, said base comprised of a baseplate and a threaded surface thereon sized to engage said threaded surface on any one of said plurality of said tips so that a single tip can be selected from said plurality of tips and said threaded base can engage on said selected tip, said threaded surfaces being positioned so that threaded rotation of said base with respect to said tip on said axis causes adjustment of length between said tip end surface of said selected tip and said baseplate so that length can be selected and adjusted by selection of a tip and by threaded interengagement between said base and said tip.

18. The vaginal dilator of claim 17 wherein said threaded surface in said tip is within a threaded recess in said tip and said threaded surface on said base is on a shank attached to said baseplate.

19. A vaginal dilator comprising:

a tip selected from a group of tips, each tip in said group of tips having a substantially cylindrical exterior surface and having an axis, each said tip having a curved tip end surface and having an attachment end opposite said curved tip end surface, each of said tips having a different length between said curved tip end surface and said attachment end, each of said tips having a threaded surface extending generally axially of said tip;

a base, said base comprised of a baseplate and a threaded surface thereon; and a spacer selected from a group of spacers of different length, said spacer having an exterior surface the size and shape of said tip and having an opening therethrough for clearing the threads interengaging between said base of said tip.

20. A vaginal dilator comprising:

a tip selected from a group of tips, each tip in said group of tips having a substantially cylindrical exterior surface and having an axis, each said tip having a curved tip end surface and having an attachment end opposite said curved tip end surface, each of said tips having a different length between said curved tip end surface and said attachment end, each of said tips having a threaded surface extending generally axially of said tip;

a base, said base comprised of a baseplate and a threaded surface thereon; and a coupler, said coupler having an axis and having an external surface in line with said external surface of said tip when said tip and said coupler are axially aligned, said coupler having a threaded surface thereon for engagement with said tip and a threaded surface thereon for engagement with said base so that said coupler can be inserted between said tip and said base to extend the length between said tip end surface and said baseplate.

21. The vaginal dilator of claim 20 wherein said threaded surface on said coupler is within a threaded recess in said tip and said threaded surface on said base is on a shank attached to said baseplate.

22. A vaginal dilator comprising:

a tip selected from a group of tips, each tip in said group of tips having a substantially cylindrical exterior surface and having an axis, each said tip having a curved tip end surface and having an attachment end opposite said curved tip end surface, each of said tips having a different length between said curved tip end surface and said attachment end, each of said tips having a threaded surface extending generally axially of said tip; and a base, said base comprised of a baseplate and a threaded surface thereon sized to engage said threaded surface on said tip so that said threaded base can engage said threaded tip, said base being selected from a group of bases each having a baseplate of different size, said threaded surfaces being positioned so that threaded rotation of said base with respect to said tip on said axis causes adjustment of length between said tip end surface and said baseplate so that length can be selected and adjusted by selection of a tip and by threaded interengagement between said base and said tip.

* * * * *